United States Patent [19]

Niederer et al.

[11] 4,450,592
[45] May 29, 1984

[54] JOINT SOCKET FOR A HIP JOINT PROSTHESIS

[75] Inventors: Peter G. Niederer, Zollikofen; Otto Frey, Winterthur, both of Switzerland

[73] Assignee: Sulzer Brothers Limited, Winterthur, Switzerland

[21] Appl. No.: 338,195

[22] Filed: Jan. 8, 1982

[30] Foreign Application Priority Data

Feb. 20, 1981 [CH] Switzerland .................. 1133/81

[51] Int. Cl.³ .............................................. A61F 1/04
[52] U.S. Cl. .................................... 3/1.912; 3/1.913; 128/92 C
[58] Field of Search .................. 3/1.91, 1.912, 1.913; 128/92 C, 92 CA

[56] References Cited

U.S. PATENT DOCUMENTS 3,840,904 10/1974 Tronzo ................................ 3/1.912

FOREIGN PATENT DOCUMENTS 2807289 8/1979 Fed. Rep. of Germany ....... 3/1.912
2225924 12/1974 France ................................ 3/1.912

*Primary Examiner*—Richard J. Apley
*Assistant Examiner*—David J. Isabella
*Attorney, Agent, or Firm*—Kenyon & Kenyon

[57] ABSTRACT

The socket body has an exterior surface which tapers in one direction while anchoring beads on the exterior surface taper in an opposite outward direction. The beads serve to anchor the body within a pelvis. In addition, cross ribs are formed on the anchoring beads with at least some of the ribs being elastic. Upon insertion of the socket, the ribs bend in a direction opposite to the direction of insertion. The two oppositely directed anchoring tapers of the socket body and the beads provide a firm fit of the socket body in a pelvis with a cement-free anchoring. Also, the bent ribs tend to resist withdrawal of the socket from the pelvis.

7 Claims, 2 Drawing Figures

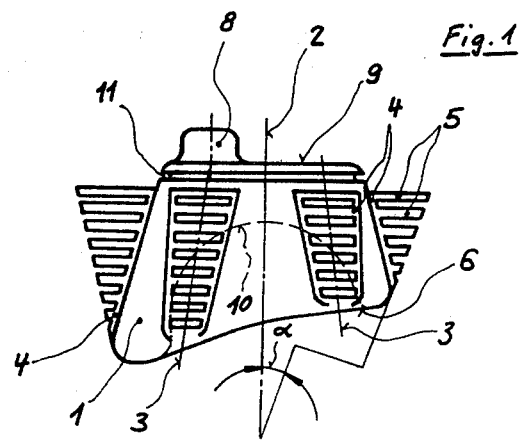
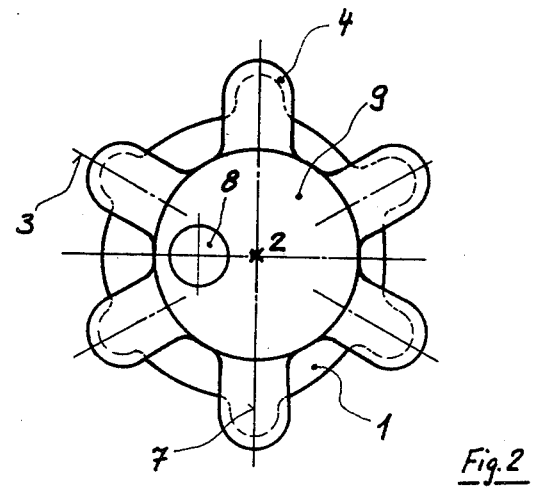

JOINT SOCKET FOR A HIP JOINT PROSTHESIS

This invention relates to a joint socket for a hip joint prosthesis.

As is known, various types of joint sockets have been anchored in a pelvis in order to receive a spherical joint head of a hip joint prosthesis. In some cases, the sockets have been constructed in a spherical shape and have been provided with external ribs or recesses for implanting in the pelvis. In other cases, for example as described in Swiss Patent Application No. 3255/80, it has been known to form a socket with a body which is tapered on the exterior surface and which is provided with protruding relief-type anchoring beads which are distributed over the circumference of the body and extend along a generatrix. In addition, the beads have been provided with ribs which are arranged crosswise to the generatrix. However, it has been found in many cases that the various types of joint sockets have not been securely fixed within the pelvis, particularly in those instances where the anchorage has been cement-free.

Accordingly, it is an object of the invention to improve the mounting of a joint socket in a pelvis in a cement-free manner.

It is another object of the invention to provide a joint socket which can be securely fixed within a pelvis for receiving a hip joint prosthesis.

Briefly, the invention provides a joint socket for a hip joint prosthesis which is constructed of a one piece body with tapering anchoring beads and elastic cross ribs. In particular, the body is provided with an internal socket which is disposed about an axis of rotation and with an exterior surface which tapers inwardly towards one end of the body symmetrically of the axis of rotation. In addition, the anchoring beads project from the exterior surface with each anchoring bead having an outwardly increasing width in a direction towards the smaller end of the socket body. For example, the anchoring beads are shaped and sized to widen conically relative to the axis of rotation of the socket body. Likewise, the cross ribs increase in size in a direction opposite to the inward taper of the socket body and, thus, the direction of insertion of the socket body into a pelvis.

Upon insertion of the socket into a bearing which has been prepared in a pelvis, the elastic cross ribs bend counter to the direction of insertion. The elastic ribs thus form a plurality of abutments against withdrawal or extraction of the socket body opposite to the direction of insertion. Further, once in place, the opposing taper of the socket body and the anchoring beads prevent additional movements in and counter to the direction of insertion. Thus, the danger of the socket becoming loose is considerably reduced.

The bearing for the pelvis in the socket can be effected, for example, by first cutting out of the bone, as exactly as possible, a space corresponding to the exterior of the basic form of the socket body. Cavities for the widening anchoring beads can then be drilled into the cut out space, again as exactly as possible, for example, using a drill which is fixed in a set position to the cut out space. For exactly centering the drill, it may be advantageous to apply an eccentrically located means on the socket body for establishing a mounting position for the body.

The angle of taper for the widening anchoring beads depends on the material of the socket. One essential factor, among others, is the elasticity of the socket material. For example, the angle defined by the widening beads to the axis of rotation may be between 1° and 20°.

The preferred material for the joint socket is a high molecular weight polyethylene of the first classification HDPE and UHMW. For this material, a conically tapering angle of from 5° to 15° is especially advantageous for the widening of the anchoring beads. In addition, an especially firm fit of the socket in a pelvis is obtained if the thickness of each rib is from 0.3 to 1.5 millimeters with a spacing between adjacent ribs of from 0.5 to 2.5 millimeters.

These and other objects and advantages of the invention will become more apparent from the following detailed description taken in conjunction with the accompanying drawings wherein:

FIG. 1 illustrates a side view of a joint socket constructed in accordance with the invention; and FIG. 2 illustrates a top view of the joint socket taken in the direction of the axis of rotation of the socket cavity.

Referring to FIG. 1, the joint socket has a body 1 with an exterior surface which is basically in the form of a rotation-symmetrical truncoconical surface with an axis of symmetry 2. In addition, the body has an internal socket 10 of spherical shape which is disposed about the axis of symmetry 2 such that the axis of symmetry also forms an axis of rotation for the arc of a circle generating the socket 10. As indicated, the socket body 1 is provided with a non-symmetrical edge about the socket 10.

Referring to FIGS. 1 and 2, the exterior surface of the body tapers inwardly towards one end symmetrically of the axis of rotation 2. In addition, the surface has a plurality of anchoring beads 4 projecting therefrom. Each of these beads 4 has an outwardly increasing width in a direction towards the smaller end of the body as indicated in FIG. 1. Each bead 4 extends along a generatrix 3 of the exterior surface of the body in relief fashion with all of the beads 4 being distributed evenly over the periphery of the body 1. For example, as indicated in FIG. 2, the body is provided with six equispaced beads 4 about the axis of symmetry 2.

As indicated in FIG. 1, each bead 4 widens opposite to the conical taper of the exterior surface of the body 1. That is, each bead has an outer surface which forms an angle $\alpha$ of inclination relative to the axis of symmetry 2. In the case where the socket is made of polyethylene, the angle is about 10°. Depending upon the elasticity of the material of the socket, the angle of inclination may vary between 1° and 20°, the optimum value for each type of material being determined experimentally.

Referring to FIG. 1, each bead 4 is provided with a plurality of transversely disposed lobe type ribs 5. These ribs 5 are disposed cross wise to the generatrix 3 and are of a length and, hence, elasticity, which increases in the direction of the widening of the anchoring beads 4, as viewed in FIG. 1. The spaces between the ribs 5 serve for an additional enlargement of the anchoring surface and for the growing in of spongy bone tissue.

As viewed in FIG. 1, the edge 6 of the socket is non-symmetrical relative to a median plane 7 (see FIG. 2) through the axis of symmetry 2 and extends farther down on one side than on the other. This forces the socket to assume a certain mounting position in a pelvis. Since the shape of the socket body 1, including the anchoring beads 4, is rotation-symmetrical, an eccentrically located means in the form of a pin 8 is disposed on the upper base area 9 of the body for establishing a mounting position for the socket. The pin 8 or a recess in the pelvis for receiving the pin 8 may, at the same time, serve as a fixed point for the centering of a drill for making holes or recesses for receiving the anchoring beads 4 in the pelvis.

As shown in FIG. 1, the anchoring beads 4 terminate below the base area 9 of the socket body 1 and an annular groove 11 is provided in the bead-free portion of the outer surface of the socket body 1. This groove 11 may be used to accommodate a metal wire in order to mark the socket position in an x-ray photo of an implanted socket.

Before inserting a joint socket, the pelvis is operatively prepared by first cutting as exactly as possible a space in the bone corresponding to the exterior shape of the socket body 1. Next, cavities are drilled in the cut-out space in order to receive the anchoring beads 4. Use may be made of a drill which is fixed in a certain position relative to the cut-out space. The insertion of the socket in the pelvis can then be effected in known manner so that the half shown to the left in FIG. 1 is arranged with the pin 8 in a lateral-cranial position in the body while the right half comes to rest in the medial-caudal direction.

Of note, the socket body 1 may be of other exterior shapes. For example, the socket body may have an outer semicircular shape or may be in the form of a truncated pyramid.

The invention thus provides a socket for a hip joint prosthesis which can be reliably anchored in place in a cement-free manner.

What is claimed is:

1. A joint socket for a hip joint prosthesis comprising
   a body having an internal socket disposed about an axis of rotation and an exterior surface tapering inwardly towards one end symmetrically of said axis;
   a plurality of anchoring beads projecting from said exterior surface, each bead being of an outwardly increasing width in a direction towards said one end to widen conically relative to said axis of rotation; and
   a plurality of ribs in each said bead disposed transversely to said axis, at least some of said ribs being elastic.

2. A joint socket as set forth in claim 1 wherein each said bead widens conically relative to said axis of rotation on an angle of between 1 to 20 degrees.

3. A joint socket as set forth in claim 2 wherein said body is made of polyethylene and said angle is from 5 to 15 degrees.

4. A joint socket as set forth in claim 3 wherein each rib is of a thickness of from 0.3 to 1.5 millimeters and is spaced from an adjacent rib of from 0.5 to 2.5 millimeters.

5. A joint socket as set forth in claim 1 which further comprises an eccentrically located means on said body for establishing a mounting position for said body.

6. A joint socket for a hip joint prosthesis comprising
   a body having an internal socket disposed about an axis of rotation and an exterior surface tapering inwardly towards one end symmetrically of said axis;
   a plurality of anchoring beads projecting radially from said exterior surface between said ends, each bead being of an outwardly increasing width in a direction towards said one end to widen conically relative to said axis of rotation; and
   a plurality of ribs in each said bead disposed transversely to said axis, at least some of said ribs being elastic.

7. A joint socket for a hip joint prosthesis comprising
   a body having an internal socket disposed about an axis of rotation and an exterior trunco-conical surface tapering inwardly towards one end symmetrically of said axis;
   a plurality of anchoring beads projecting from said exterior surface, each bead being disposed on a generatrix of said body and being of an outwardly increasing width in a direction towards said one end to widen conically relative to said axis of rotation; and
   a plurality of ribs in each said bead disposed transversely to said axis, at least some of said ribs being elastic.

* * * * *